US012708625B2

(12) United States Patent
Choi et al.

(10) Patent No.: US 12,708,625 B2
(45) Date of Patent: Aug. 18, 2026

(54) PHARMACEUTICAL COMPOSITION FOR IMPROVING OR TREATING POST-SURGICAL HYPOPARATHYROIDISM AND TREATMENT METHOD USING THE SAME

(71) Applicant: DONGGUK UNIVERSITY INDUSTRY-ACADEMIC COOPERATION FOUNDATION, Seoul (KR)

(72) Inventors: Han Seok Choi, Seoul (KR); Yun Sung Lim, Goyang-si (KR); Kwang Joon Kim, Seoul (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 1007 days.

(21) Appl. No.: 17/634,644

(22) PCT Filed: May 13, 2020

(86) PCT No.: PCT/KR2020/006293

§ 371 (c)(1),
(2) Date: Feb. 11, 2022

(87) PCT Pub. No.: WO2021/029517

PCT Pub. Date: Feb. 18, 2021

(65) Prior Publication Data

US 2022/0288076 A1 Sep. 15, 2022

(30) Foreign Application Priority Data

Aug. 13, 2019 (KR) ........................ 10-2019-0099136
May 7, 2020 (KR) ........................ 10-2020-0054814

(51) Int. Cl.
*A61K 31/517* (2006.01)
*A61K 9/00* (2006.01)
*A61P 5/18* (2006.01)

(52) U.S. Cl.
CPC ............. *A61K 31/517* (2013.01); *A61P 5/18* (2018.01); *A61K 9/0053* (2013.01)

(58) Field of Classification Search
CPC ................................ A61K 31/517; A61P 5/18
See application file for complete search history.

(56) References Cited

U.S. PATENT DOCUMENTS 6,417,215 B1 7/2002 Lago
2005/0032850 A1 2/2005 Del et al.

FOREIGN PATENT DOCUMENTS

WO 2004041755 A2 5/2004
WO 2004056365 A2 7/2004
WO WO-2008107390 A1 * 9/2008 ......... A61K 31/4184

OTHER PUBLICATIONS

Hypoparathyroidism Al-Azem et al. Best Practice & Research Clinical Endocrinology & Metabolism 26 (2012) 517-522 (Year: 2012).*
Short and long-term impact of parathyroid autotransplantation on parathyroid function after total thyroidectomy Hicks et al. Gland Surg 2017;6(Suppl 1):S75-S85 (Year: 2017).*
International Search Report and Written Opinion corresponding to PCT/KR2020/006293; dated Sep. 1, 2020 (10 pages).

* cited by examiner

*Primary Examiner* — Jeffrey S Lundgren
*Assistant Examiner* — Eric Tran
(74) *Attorney, Agent, or Firm* — DILWORTH IP, LLC

(57) ABSTRACT

The present invention relates to a pharmaceutical composition for improving or treating hypoparathyroidism caused by damage to parathyroid tissue and vascular tissue around the parathyroid gland due to surgery around the neck, and a method for treating post-surgical hypoparathyroidism using the same, and the composition can promote secretion of parathyroid hormone by containing a calcium-sensing receptor antagonist as an active ingredient to help the restoration of damaged parathyroid tissue through neovascularization and angiogenesis, and furthermore, can alleviate hypocalcemia, hyperphosphatemia, and hypercalciuria by increasing the concentration of blood parathyroid hormone to a normal range level. Administration of the composition can improve the quality of life of patients with hypoparathyroidism.

1 Claim, 7 Drawing Sheets

[Fig. 1]
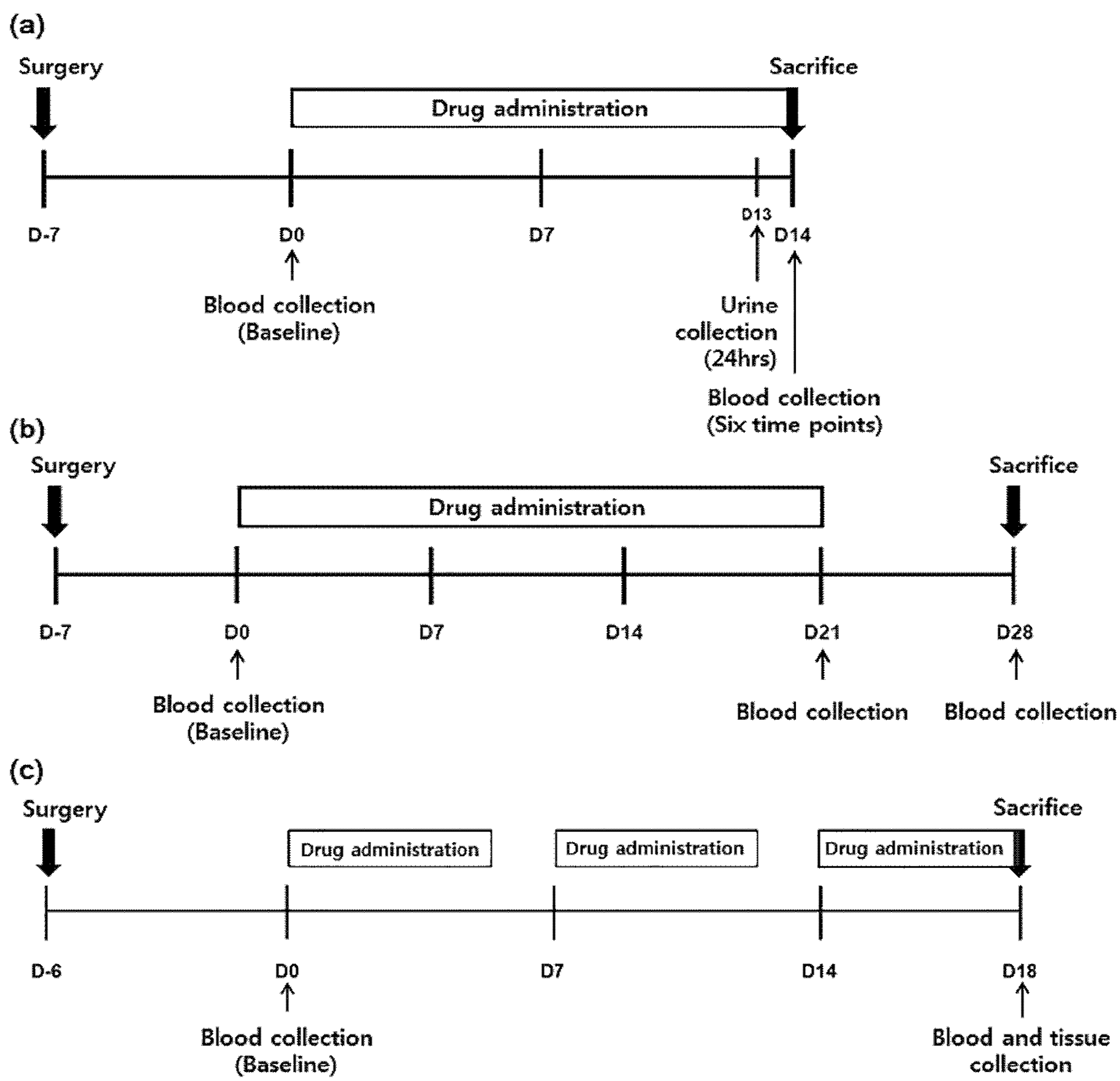

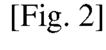
[Fig. 2]
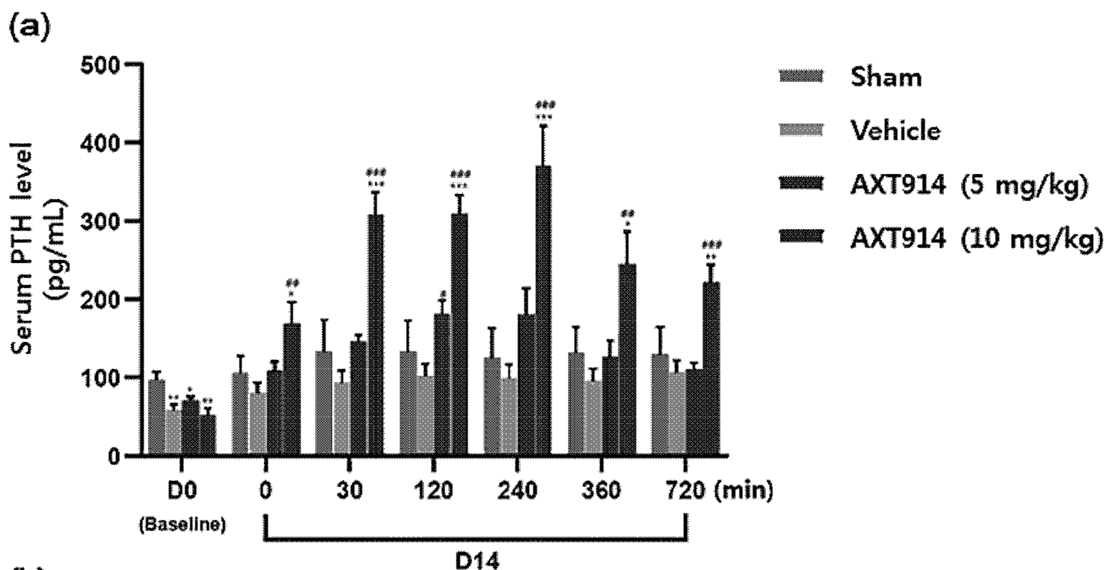
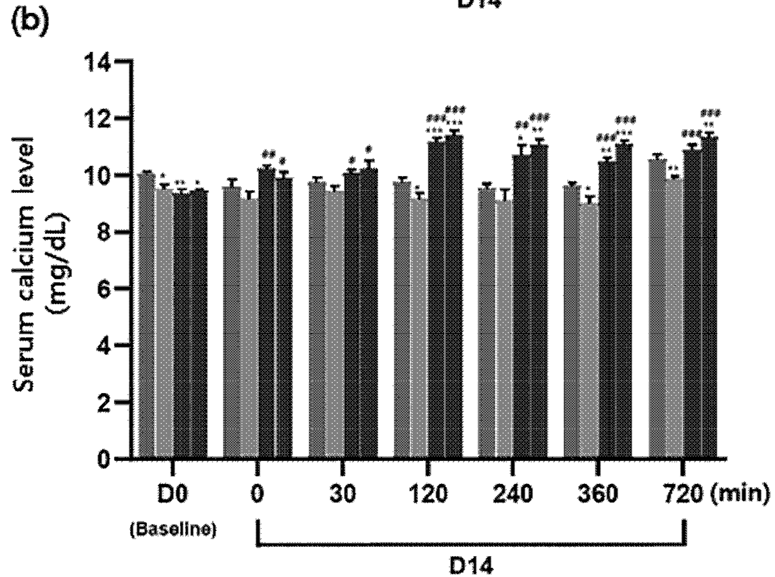
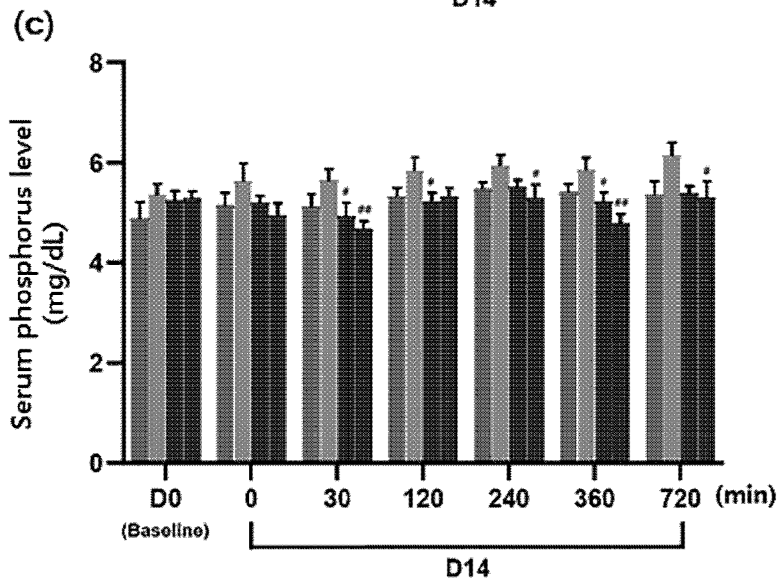

[Fig. 3]
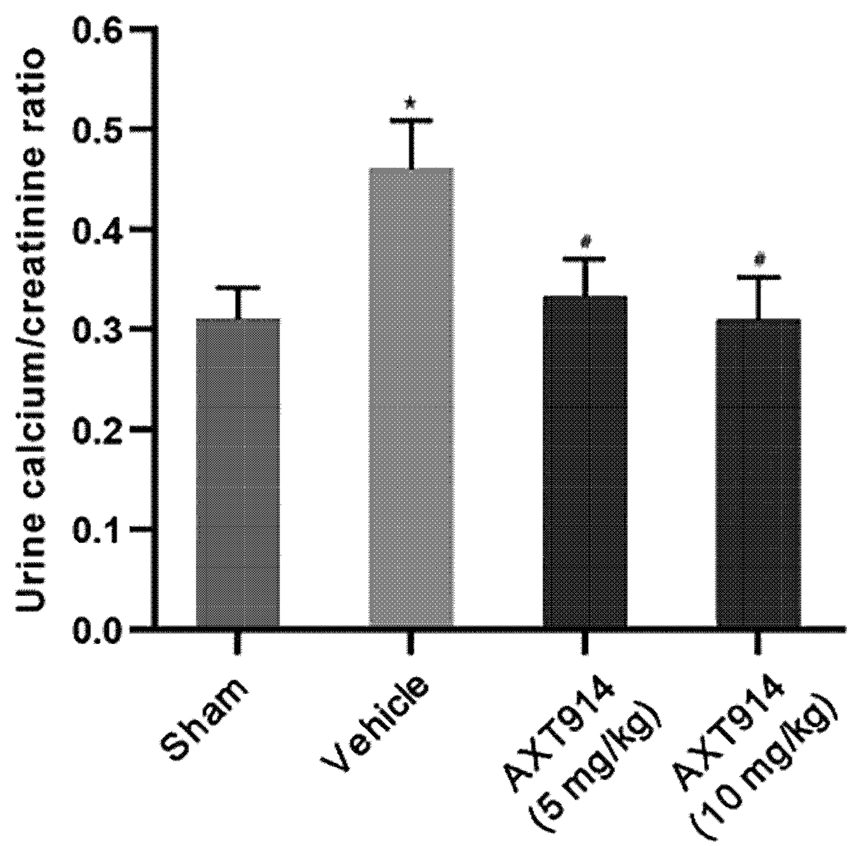

[Fig. 4]
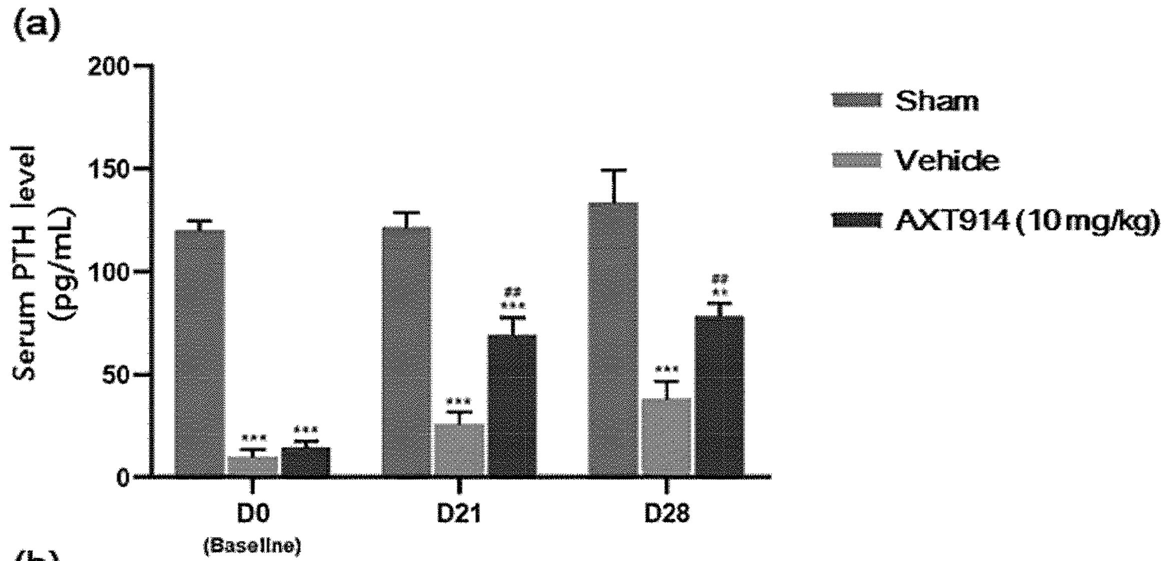
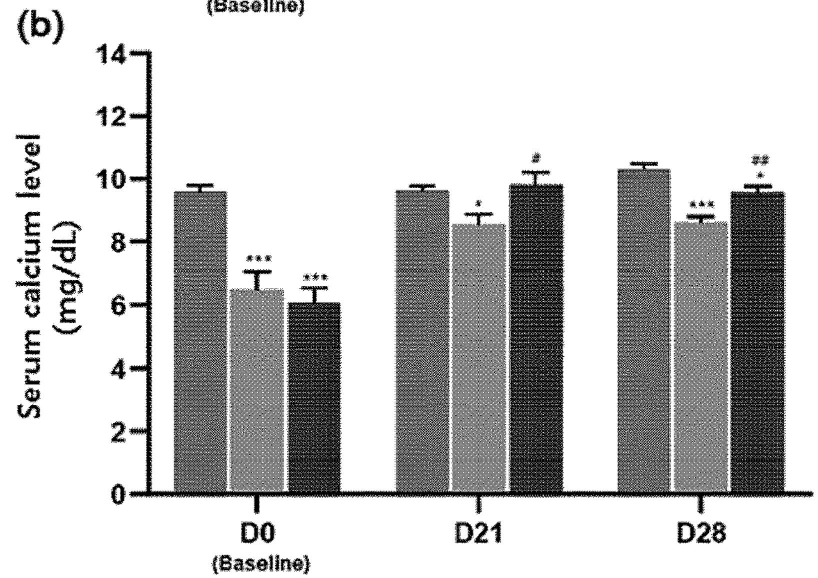
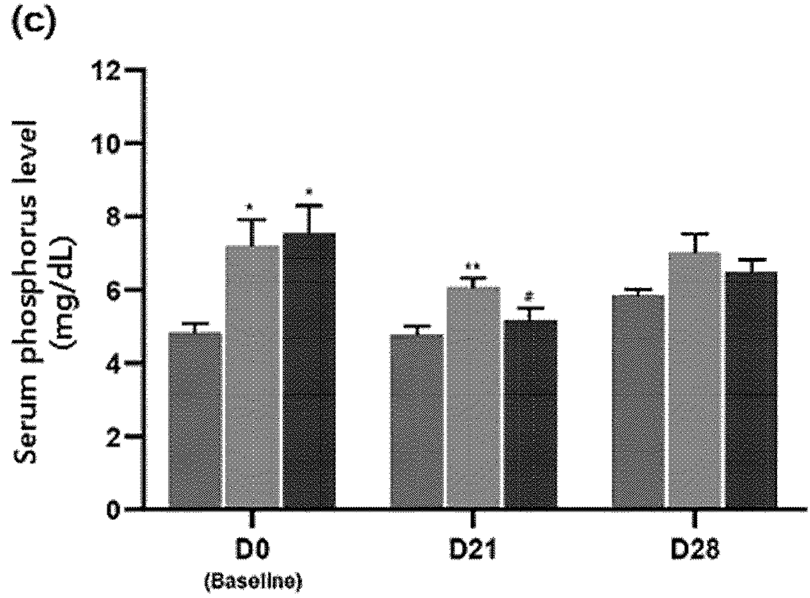

[Fig. 5]
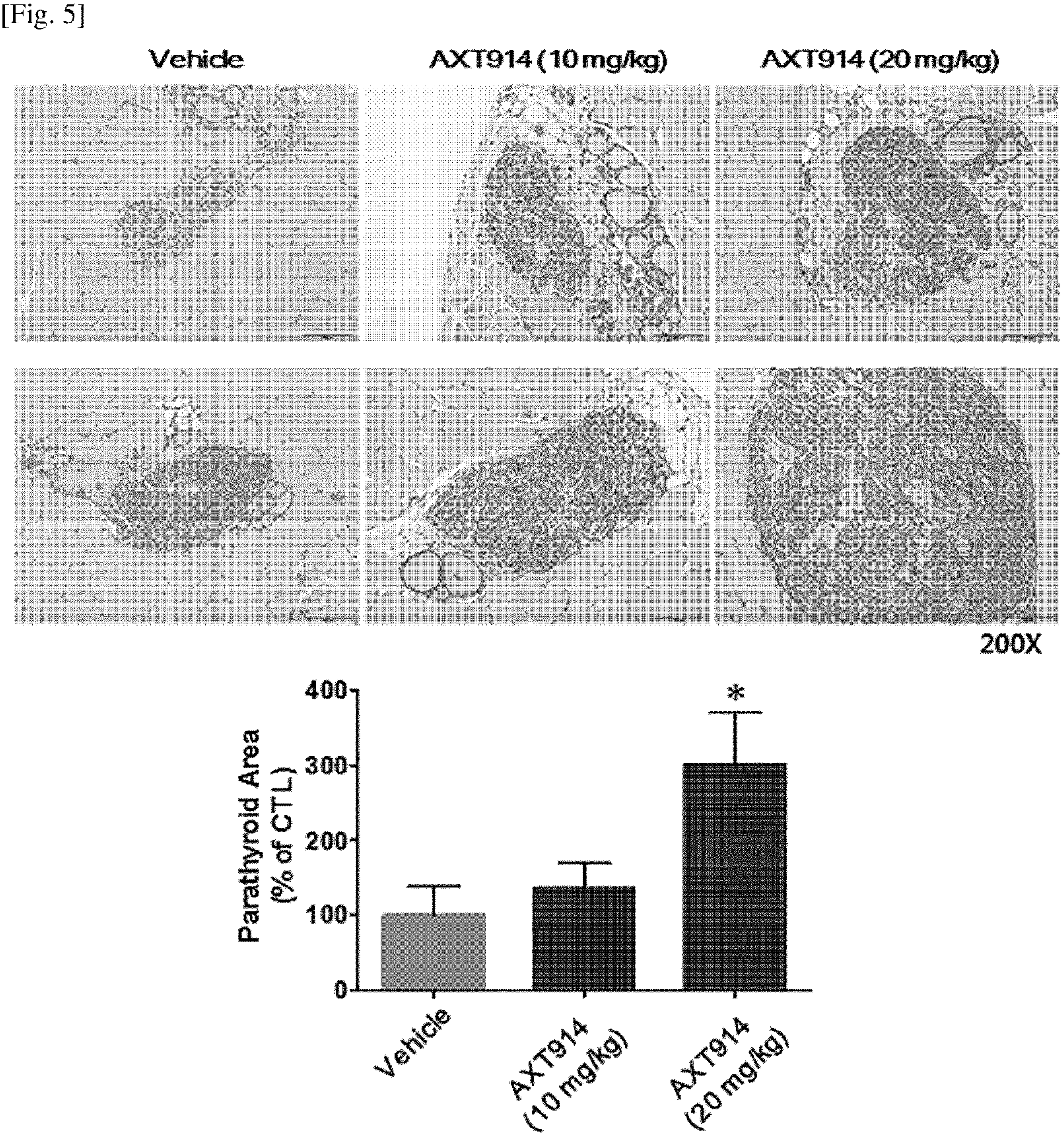

[Fig. 6a]
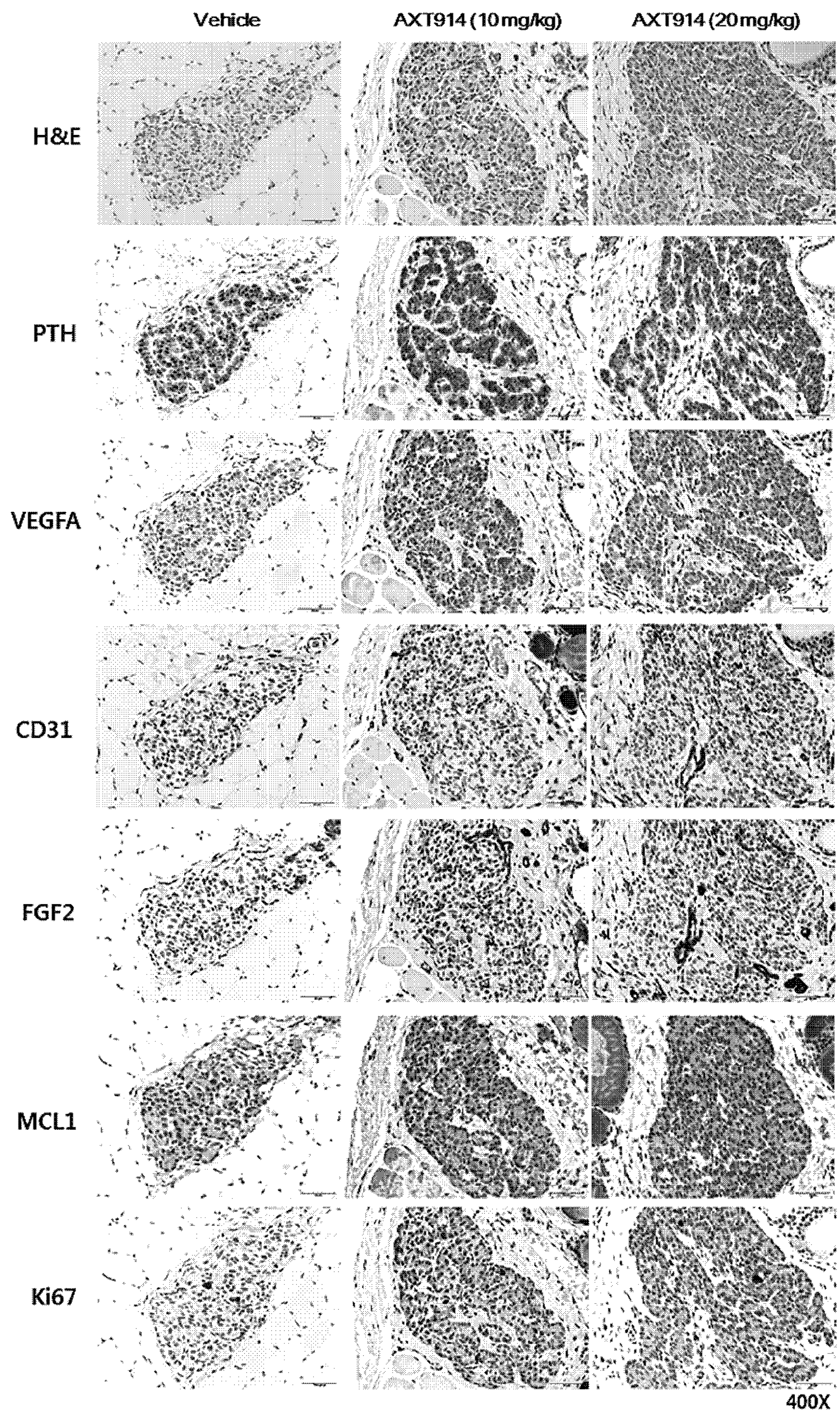

[Fig. 6b]
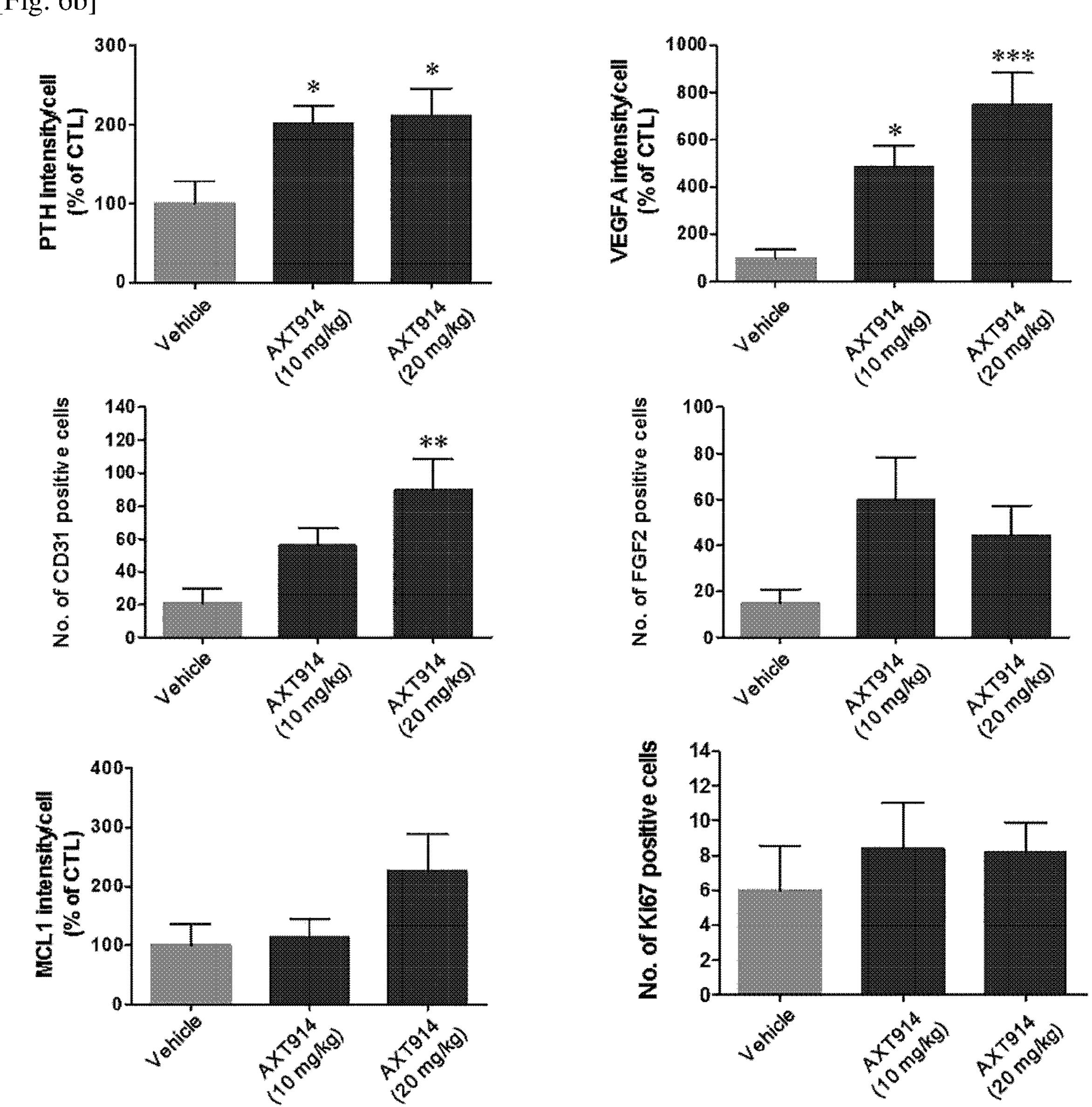

PHARMACEUTICAL COMPOSITION FOR IMPROVING OR TREATING POST-SURGICAL HYPOPARATHYROIDISM AND TREATMENT METHOD USING THE SAME

CROSS REFERENCE TO RELATED APPLICATIONS

This application is a 35 U.S.C. § 371 national stage application of PCT International Application No. PCT/KR2020/006293, filed May 13, 2020, which claims priority from Korean Patent Application Nos. 10-2019-0099136, and 10-2020-0054814, filed Aug. 13, 2019, and May 7, 2020, respectively, the contents of which are incorporated herein in their entireties by reference. The above-referenced PCT International Application was published in the English language as International Publication No. WO 2021/029517 A1 on Feb. 18, 2021.

TECHNICAL FIELD

The present invention relates to a pharmaceutical composition for improving or treating hypoparathyroidism caused by damage to parathyroid tissue and vascular tissue around the parathyroid gland due to surgery around the neck, and a method for treating post-surgical hypoparathyroidism using the same.

BACKGROUND ART

Post-surgical hypoparathyroidism is caused by the removal of some or all of the parathyroid glands or damage to blood vessels supplying bloodstream to the parathyroid gland during surgery around the neck such as surgery of the thyroid gland, is the most common complication occurring after surgery of the thyroid gland, and also occurs in a significant proportion of patients who have had other neck surgeries. This biochemical feature is characterized in that hypocalcemia, hyperphosphatemia, and the like may occur and calcium excretion is increased through urine because the parathyroid hormone (PTH) level is undetectable or is too low to reach an appropriate level. Hypoparathyroidism following surgery is usually a transient phenomenon, but is considered to become permanent if the symptom persists for more than 6 months or more than 1 year after surgery. Meta-analysis results based on statistical studies show that transient hypoparathyroidism affects 19 to 38% of patients who underwent thyroidectomy, while permanent hypoparathyroidism occurs only in up to 3% of patients who underwent thyroidectomy. However, other researchers insist that the true prevalence of hypoparathyroidism may be underestimated due to several reasons such as insufficient definitions, failure to follow-up the disease persistently, and conflicts of interest. In fact, some studies have reported that a prevalence of permanent hypoparathyroidism after surgery goes up to 12%.

The conventional management method of post-surgical hypoparathyroidism is to supplement large amounts of calcium and vitamin D for life, which may maintain the concentration of blood calcium at a normal level or slightly below the normal level and ameliorate symptoms of hypocalcemia such as muscle spasms, numbness, and tingling sensation, but may increase a risk such as hypercalciuria, kidney stones, and ectopic calcification. Further, supplementing calcium and vitamin D in high dose may rather negatively affect the recovery of damaged parathyroid glands. Calcium and vitamin D suppress the secretion of parathyroid hormone (PTH) by binding to a calcium-sensing receptor (CaSR) and a vitamin D receptor, respectively in parathyroid cells, and particularly, high concentrations of vitamin D may induce parathyroid cell death.

CaSR is a G protein receptor expressed mainly in parathyroid cells, and regulates PTH secretion by sensing the concentration of $Ca^{2+}$ in blood. The human calcium-sensing receptor consists of 1,078 amino acids, and its expression in the kidneys, thyroid C cells, brain, and bone marrow cells has been reported in addition to the parathyroid gland. When CaSR binds to the ligand $Ca^{2+}$, inositol triphosphate is produced and intracellular $Ca^{2+}$ concentration is increased by working with the G protein to activate phospholipase C, resulting in suppression of PTH secretion. A material which serves as a CaSR regulator inhibiting the action of CaSR is a CaSR antagonist or calcilytic. CaSR antagonists that bind to CaSR on the surface of parathyroid cells reduce intracellular $Ca^{2+}$ concentration and antagonize the suppressive signal for PTH secretion, and as a result, it was expected that PTH would be overexpressed and the effect of promoting bone formation would appear. Based on these characteristics of CaSR antagonists, some CaSR antagonists with a short half-life have been developed for the treatment of osteoporosis, and some of them have been clinically tested in humans. However, CaSR antagonists have no effect on improving bone density in humans, and none have succeeded due to safety concerns regarding hypercalcemia. Further, the effects of CaSR antagonists on artificially damaged parathyroid tissue, such as post-surgical hypoparathyroidism, have not been known.

Accordingly, the present inventors completed the present invention relating to a pharmaceutical composition for alleviating or treating post-surgical hypoparathyroidism, containing a CaSR antagonist as an active ingredient and a method for treating post-surgical hypoparathyroidism using the same by confirming the effects of restoring the functions of damaged parathyroid tissues by CaSR antagonists, such as an increase in PTH secretion, and normalization of calcium and phosphorus homeostasis using a model in which the parathyroid gland was partially removed by artificial surgery (hemi-parathyroidectomy model) and a model in which the removed parathyroid gland was re-transplanted (total parathyroidectomy and autotransplantation model).

DISCLOSURE OF INVENTION

Technical Problem

An object of an aspect of the present invention is to provide a pharmaceutical composition for improving or treating post-surgical hypoparathyroidism, containing a calcium-sensing receptor antagonist as an active ingredient.

Here, the calcium-sensing receptor antagonist may be a compound of Formula 1.

The composition may further contain a pharmaceutically acceptable carrier, adjuvant or diluent.

The composition may increase the secretion of parathyroid hormone.

In addition, an object of another aspect of the present invention is to provide a method for treating post-surgical hypoparathyroidism, the method including administering the composition to a mammal in need of functional restoration of a parathyroid gland damaged by surgery.

Here, the administration may be such that the composition is orally administered at a concentration of 1 to 30 mg/mL.

The method may increase the concentration of blood parathyroid hormone.

Solution to Problem

According to an exemplary embodiment of the present invention, the present invention provides a pharmaceutical composition for improving or treating post-surgical hypoparathyroidism, containing a calcium-sensing receptor antagonist as an active ingredient.

The most common cause of hypoparathyroidism is the case where hypoparathyroidism is caused by the removal of some or all of the parathyroid glands located just behind the thyroid together during thyroid surgery. Other causes are largely divided into congenital and acquired causes, and as the congenital causes, there are not only cases where hypoparathyroidism independently occurs, but also cases where hypoparathyroidism occurs with various other congenital diseases such as DiGeorge syndrome. The present invention is provided to alleviate or treat hypoparathyroidism caused by surgery, and is characterized by using a calcium-sensing receptor antagonist to restore the function of damaged parathyroid gland.

The calcium-sensing receptor (CaSR) antagonist is a drug that acts as a regulator of CaSR inhibiting CaSR activity, and induces PTH overexpression by binding to CaSR on the surface of parathyroid cells to block signals suppressing PTH secretion. In the present invention, it was confirmed through experiments that when some of the parathyroid glands are removed during surgery or the removed parathyroid gland is re-transplanted, a CaSR antagonist helps the restoration of parathyroid tissue through neovascularization and angiogenesis to restore parathyroid secretory functions such as PTH secretion to normal or higher levels.

As the CaSR antagonist, a material known in the art may be used without limitation, and as an example, the material may be a selective estrogen receptor modifier (SERM), bisphosphonate, parathyroid hormone (PTH) and segments and analogs thereof, estrogen, calcitonin, synthetic steroids, synthetic isoflavones, vitamin D derivatives, vitamin K derivatives, strontium salts, a cathepsin K inhibitor, an $\alpha v\beta 3$ integrin (Vitronectin) antagonist, a prostaglandin E2 (PGE2) receptor agonist, a receptor activator of nuclear factor-κB ligand (RANKL) inhibitor, and the like. The present invention is characterized by using a compound represented by the following Formula 1 as a CaSR antagonist. The following compound of Formula 1 is a CaSR antagonist for treating osteoporosis and has excellent solubility during microemulsion preconcentration.

[Formula 1]

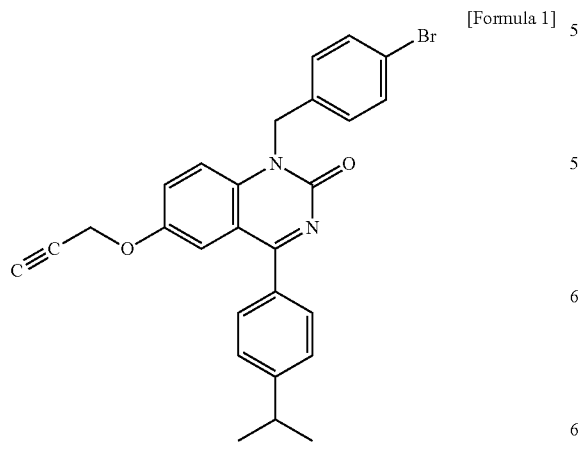

A composition containing the CaSR antagonist may be mixed with pharmaceutically typically used carriers and diluents, other pharmaceutically typically used adjuvants, and the like and formulated in the form of a pharmaceutically typically acceptable formulation, thereby preparing a pharmaceutical formulation. When the composition is formulated, the composition is prepared using a commonly used diluent or vehicle such as a filler, an extender, a binder, a wetting agent, a disintegrant, and a surfactant. Examples of the carrier, the diluent, and the adjuvant include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like.

The form of the formulation may be in the form of an oral dosage form such as a powder, a granule, a tablet, a capsule, a suspension, an emulsion, a syrup, and an aerosol, or an external preparation, a suppository, and a sterile injection solution. A solid formulation for oral administration may include a tablet, a pill, a powder, a granule, a capsule, and the like, and a liquid preparation for oral administration correspond to a suspension, a liquid for internal use, an emulsion, a syrup, and the like. Examples of a formulation for parenteral administration include an aqueous sterile solution, a non-aqueous solvent, a suspension, an emulsion, a freeze-dried preparation, and a suppository.

A method for administering the composition administers the composition in a pharmaceutically effective amount, and an effective dosage level may be determined according to factors including types of diseases of patients, the severity of disease, the activity of drugs, sensitivity to drugs, administration time, administration route, excretion rate, treatment period, and simultaneously used drugs, and other factors well known in the medical field. In order to enhance the therapeutic effect of the composition, the daily dose may be 0.5 to 50 mg/kg, preferably 1 to 30 mg/kg. The administration may be carried out once a day, and may be divided into several times a day. All routes of administration are possible, and the composition may be administered orally or by subcutaneous, intra-arterial, intravenous, intramuscular, intraperitoneal or intrasternal injection, as an example.

According to another exemplary embodiment of the present invention, the present invention provides a method for treating post-surgical hypoparathyroidism, and specifically, the method includes administering the composition to a mammal in need of functional restoration of a parathyroid gland damaged by surgery.

The mammal is a mammal including a human, and is in a state where parathyroid hormone is not secreted in a normal range because the function of the parathyroid glands does not operate normally due to the removal of some of the parathyroid glands during surgery, or the transplantation of the removed parathyroid gland. The administration of the composition to a mammal may be such that the composition is orally administered at a concentration of 1 to 30 mg/mL. When the composition is administered to the mammal, the parathyroid function is restored to promote secretion of parathyroid hormone, so that the concentration of blood parathyroid hormone may be increased.

Advantageous Effects of Invention

The composition according to the present invention can promote secretion of parathyroid hormone by containing a calcium-sensing receptor antagonist as an active ingredient to help the restoration of damaged parathyroid tissue through neovascularization and angiogenesis, and furthermore, can alleviate hypocalcemia, hyperphosphatemia, and hypercalciuria by increasing the concentration of blood parathyroid hormone to a normal range level. Administration of the composition can improve the quality of life of patients with hypoparathyroidism.

BRIEF DESCRIPTION OF DRAWINGS

FIG. 1 is a schematic view illustrating an experimental schedule of the composition according to the present invention; (a) Experimental Schedule 1 relates to administration of AXT914 in a hemi-parathyroidectomy model. One week after the hemi-parathyroidectomy, AXT914 (5 mg/kg or 10 mg/kg) or a vehicle was orally administered to rats daily for 2 weeks. Blood was collected before drug administration (Day 0; baseline), and at an interval of 0, 30, 120, 240, 360, and 720 minutes on Day 14 after the start of drug administration. Urine was collected on Day 13 after the start of drug administration. (b) Experimental Schedule 2 relates to administration of AXT914 in a total parathyroidectomy and auto-transplantation model. One week after the total parathyroidectomy and auto-transplantation, AXT914 (10 mg/kg) or a vehicle was orally administered to rats daily for 3 weeks. Blood was collected before drug administration (Day 0; baseline) and on Day 21 and Day 28 after the start of drug administration. (c) Experimental Schedule 3 relates to administration of AXT914 in a total parathyroidectomy and auto-transplantation model. Six days after the total parathyroidectomy and auto-transplantation, AXT914 (10 mg/kg or 20 mg/kg) or a vehicle was orally administered to rats 5 days weekly for 18 days. Blood was collected before drug administration (Day 0; baseline) and on Day 18 after the start of drug administration. On Day 18 after the start of drug administration, a histological analysis was performed by sacrificing the rats to isolate the sternocleidomastoid muscle (SCM) in which the parathyroid gland was transplanted.

FIG. 2 is a graph comparing the levels of serum (a) PTH, (b) calcium, and (c) phosphorus measured on Day 0 (baseline) and Day 14 after drug administration in the hemi-parathyroidectomy model of Experimental Schedule 1. The results are shown as mean±SEM and compared by one-way ANOVA and Fisher's LSD method; *: P<0.05, : P<0.01, *: P<0.001 compared to the sham surgery group, and #: P<0.05, ##: P<0.01, ###: P<0.001 compared to the vehicle administration group.

FIG. 3 is a graph comparing urinary calcium excretion (calcium/creatinine ratios) measured on Day 13 after drug administration in the hemi-parathyroidectomy model of Experimental Schedule 1. The results are shown as mean±SEM and compared by one-way ANOVA and Fisher's LSD method; *: P<0.05 compared to the sham surgery group, and #: P<0.05 compared to the vehicle administration group.

FIG. 4 is a series of graphs comparing the levels of serum (a) PTH, (b) calcium, and (c) phosphorus measured on Day 0 (baselin), Day 21, and Day 28 after drug administration in the total parathyroidectomy and auto-transplantation model of Experimental Schedule 2. The results are shown as mean±SEM and compared by one-way ANOVA and Fisher's LSD method; *: P<0.05, : P<0.01, *: P<0.001 compared to the sham surgery group, and #: P<0.05, ##: P<0.01 compared to the vehicle administration group.

FIG. 5 illustrates the results of H&E staining for SCM isolated from the total parathyroidectomy and auto-transplantation model of Experimental Schedule 3. The results for the stained parathyroid area (%) are shown as mean±SEM and compared by one-way ANOVA and Turkey's Multiple Comparison method; *: P<0.05 compared to the vehicle administration group.

FIG. 6*a* illustrates the results of H&E staining and immunohistochemical staining of PTH, VEGFA, CD31, FGF2, MCL1 and Ki67 for SCM isolated from the total parathyroidectomy and auto-transplantation model of Experimental Schedule 3. FIG. 6*b* illustrates the results for intensity (%) or cell numbers of stained PTH, VEGFA, CD31, FGF2, MCL1, and Ki67 as mean±SEM. The results are compared by one-way ANOVA and Turkey's Multiple Comparison method; *: P<0.05, : P<0.01, *: P<0.001 compared to the vehicle administration group.

BEST MODE FOR CARRYING OUT THE INVENTION

Hereinafter, a pharmaceutical composition for improving or treating post-surgical hypoparathyroidism according to the present invention and a use thereof will be described in more detail with reference to the accompanying drawings. However, such a description is suggested by way of example merely for help in understanding the present invention, and the scope of the present invention is not limited by such an exemplary description.

1. Materials and Methods 1-1. Experimental Animal 9-week-old female Wistar rats were purchased from Koatech Co., Ltd. (Korea), and housed in an SPF room at a temperature of 21 to 23° C. and a humidity of 40 to 60% using a standard cage and under 12 hours cycles of light and darkness. The rats were acclimatized to the room for 1 week while being fed with a standard laboratory feed, and then used in the experiment. All care and experiments of experimental animals were performed following the guidelines by Animal Research Institute of Medical Science at Dongguk University, and the experimental schedule was approved by the Animal Institutional Review Board (AIRB No. 2016-04149 and AIRB No. 2019-07188).

1-2. Development of Post-Surgical Hypoparathyroidism Rat Model

To construct a post-surgical hypoparathyroidism rat model, 10-week-old rats acclimatized for 1 week were used.

To identify the parathyroid gland, a photosensitization method using 5-aminolevulinic acid hydrochloride (5-ALA) was performed. Briefly, a 50 mg/mL 5-ALA solution was prepared by suspending a 5-ALA powder (Sigma-Aldrich Korea, 5-aminolevulinic acid, #A3785, purity ≥98%) in a 0.9% NaCl solution. The rats were injected intraperitoneally with 500 mg/kg of the 5-ALA solution and after 2 hours, intramuscularly with Zoletil 50 (Virbac Laboratories, France) (0.1 mL/kg of body weight) and Rompun® (Bayer, Germany) (0.1 mL/kg of body weight). The anesthetized rats were laid down and the anterior neck and chest area were disinfected with povidone-iodine. In the surgical procedure, the trachea and the thyroid glands were exposed by incising the skin longitudinally from the midline of the neck. Both parathyroid glands showing a red fluorescent color were identified using blue light with a wavelength of 405±3 nm (Ergonomic LED Light Sources, Ocean Optics Inc., #LS-405, USA). In the case of the hemi-parathyroidectomy model, only one of both the parathyroid glands was removed. In the case of total parathyroidectomy and auto-transplantation model, both the parathyroid glands were removed, and then cut into small pieces, put into a small pocket made in the right sternocleidomastoid muscle (SCM), and the pocket was sutured with a non-absorbable monofilament Vicryl 5-0.

1-3. AXT914 Preparation

AXT914 was obtained by Novartis Pharma AG (Switzerland). The AXT914 was prepared in the form of a microemulsion by the following method. Briefly, after Cremophor RH40 was heated to 65° C. with stirring, the Cremophor RH40, Capmul MCM, triethyl citrate, and ethanol absolute were mixed at a weight ratio of 34.6%, 42%, 8.4%, and 10%, respectively. After a clear solution obtained by stirring the mixture for 1 hour was used as a vehicle and mixed with AXT914 (weight ratio of 5%), the resulting mixture was stirred at an ambient temperature for 8 to 12 hours. A finally obtained microemulsion preconcentrate was diluted 10 folds with deionized water (DW) and mixed vigorously before administration.

1-4. Experimental Schedule

An animal experiment was performed on the hemi-parathyroidectomy model and the total parathyroidectomy and auto-transplantation model, respectively, by the experimental schedule as follows.

① Experimental Schedule 1: Administration of AXT914 in Hemi-Parathyroidectomy Model Referring to FIG. 1*a*, rats that had undergone hemi-parathyroidectomy were divided into a vehicle administration group (n=11), an AXT914 administration group 1 (n=10), and an AXT914 administration group 2 (n=11). A sham surgery group (n=9), which had undergone sham surgery, was also prepared. One week after the surgery, the AXT914 prepared in 1-3. was orally administered to the rats once daily for 2 weeks using a zonde needle. 5 mg/kg and 10 mg/kg of the AXT914 were administered to AXT914 administration groups 1 and 2, respectively. The vehicle (a mixture mixed with AXT914 in 1-3.) was orally administered to the vehicle administration group and the sham surgery group. Urine of the rats was collected for 24 hours on Day 13 after the start of drug administration. Blood was collected from the tails of the rats before the administration of drug (baseline) and from the tails of the rats at 0, 30, 120, 240, 360, and 720 minutes on Day 14 after the start of drug administration, and the rats were sacrificed.

② Experimental Schedule 2: Administration of AXT914 in Total Parathyroidectomy and Auto-Transplantation Model Referring to FIG. 1*b*, rats that had undergone total parathyroidectomy and auto-transplantation were divided into a vehicle administration group (n=8) and an AXT914 administration group (n=8). A sham surgery group (n=6), which had undergone sham surgery, was also prepared. One week after the surgery, the AXT914 prepared in 1-3. was orally administered to the rats once daily for 3 weeks using a zonde needle, and the rats were sacrificed 1 week after the completion of administration and used for analysis. 10 mg/kg of AXT914 was administered to the AXT914 administration group. The vehicle was orally administered to the vehicle administration group and the sham surgery group. Blood was collected from the tails of the rats before the administration of drug (baseline) and from the tails of the rats on Day 21 and Day 28 after the start of drug administration.

③ Experimental Schedule 3: Administration of AXT914 in Total Parathyroidectomy and Auto-Transplantation Model Referring to FIG. 1*c*, rats that had undergone total parathyroidectomy and auto-transplantation were divided into a vehicle administration group (n=11), an AXT914 administration group 1 (n=11), and an AXT914 administration group 2 (n=11). A sham surgery group (n=7), which had undergone sham surgery, was also prepared. Six days after the surgery, the AXT914 prepared in 1-3. was orally administered to the rats once daily every 5 days weekly for 18 days using a zonde needle, and the rats were sacrificed on Day 18 of the completion of administration and used for analysis. 10 mg/kg and 20 mg/kg of the AXT914 were orally administered to AXT914 administration groups 1 and 2, respectively. The vehicle was orally administered to the vehicle administration group and the sham surgery group. Blood was collected from the tails of the rats before the administration of drug (baseline) and collected from the tails of the rats on Day 18 of the completion of drug administration. A histological analysis was performed by sacrificing the rats to isolate SCMs with parathyroid glands autotransplanted.

1-5. Biochemical Analysis

Serum samples obtained by centrifugation of BD Microtainer SSTTM (prod. No. REF 365967, Becton Dickinson) containing blood, and were stored in a −80° C. deep freezer. Parathyroid hormone (PTH) levels were measured by a spectrophotometer using the PTHELISA kit (rat intact PTH ELISA kit, Immutopics, Inc., #60-2500, USA). Serum calcium and phosphorus levels were measured by a 5-nitro-5'-methyl-BAPTA method and a molybdate UV method, respectively using cobas c 702 (Roche Diagnostics, IN). Urine calcium and creatinine levels were measured by a 5-nitro-5'-methyl-BAPTA method and a rate-blanked compensated kinetic Jaffe method, respectively using cobas c 702 (Roche Diagnostics, IN).

1-6. Histological Analysis

SCM tissues were collected from the AXT914 administration group and the vehicle administration group and fixed in 4% neutral buffered formalin for 24 hours. After the tissues were embedded in paraffin and cut into a thickness of 4 um, Hematoxylin (Sigma-Aldrich, #HHS32, USA) and Eosin Y (Sigma-Aldrich, ZE6003, USA) stainings were performed. Photographs were taken of each slide at 200 and 400 magnification.

To confirm expression of PTH, vascular endothelial growth factor A (VEGFA), CD31, a basic fibroblast growth factor (FGF2), MCL1, and Ki67 in transplanted parathyroid tissues, immunohistochemical staining was performed using antibodies against each specific antigen PTH (Cloud-Clone Corp., #PAA866 Ra01, USA), VEGFA (Abcam®, #ab1316, UK), CD31 (Abcam®, #ab182981), FGF2 (Santa Cruz, #sc-74412, USA), MCL1 (Abcam®, #ab32087), and Ki67 (Abcam®, #ab15580), secondary antibodies anti-Mouse-HRP (Abcam®, ab205719) and anti-Rabbit-HRP (Abcam®, ab205718), and a 3, 3'-diaminobenzidine (DAB) coloring reagent (Liquid DAB B Substrate Chromogen System, Dako North America Inc., #K3468, USA). Photographs were taken of each slide at 200 and 400 magnification with Olympus BX53F (Olympus, Japan), and antibodies were detected using a digital image processing and analysis software LEICA Qwin V3 (Leica Microsystems Imaging Solutions Ltd., UK).

1-7. Statistical Analysis

All statistical analyses were performed using SPSS version 20.0 (SPSS Inc., IL). The Data from experimental result are shown as mean±standard error (SEM). In the biochemical analysis on blood, comparison between administration groups was performed by one-way ANOVA and Fisher's least significant difference (LSD). In the immunohistochemical analysis, a repeated analysis ANOVA was performed to determine a significant difference between administration groups, and then a multiple comparison was derived by Turkey's Multiple Comparison method. The results were considered statistically significant when $P<0.05$.

2. Result 2-1. Effects of AXT914 in Hemi-Parathyroidectomy Model (Experimental Schedule 1)

Using rat blood collected before drug administration as a baseline, serum PTH, calcium, and phosphorus levels of the sham surgery group, the vehicle administration group, and the AXT914 administration groups were compared on Day 14 after the start of drug administration, and the results were illustrated in FIG. 2.

The PTH levels of AXT914 administration group 1 was higher than that of the vehicle administration group at 120 minutes, but there was no statistical difference from the sham surgery group. In contrast, PTH levels in AXT914 administration group 2 were significantly higher than those in the other groups at all times.

AXT914 administration groups 1 and 2 had significantly higher calcium levels than those of the vehicle administration group at all times. However, the calcium levels of AXT914 administration group 1 and AXT914 administration group 2 had no statistical difference from those of the sham surgery group at 0, 30, and 720 minutes and 0, and 30 minutes, respectively.

AXT914 administration groups 1 and 2 had decreased phosphorus levels during most of the time, but had no statistical difference from the sham surgery group. The phosphorus levels of AXT914 administration group 1 and ATX914 administration group 2 were significantly lower at 30, 120, and 360 minutes and 30, 240, 360, and 720 minutes, respectively than those of the vehicle administration group.

Urine calcium excretion was measured for 24 hours on Day 13 after drug administration, and the ratios of calcium/creatinine in the sham surgery group, the vehicle administration group and the AXT914 administration groups were compared, and the results were illustrated in FIG. 3.

The vehicle administration group had a significantly higher urine calcium/creatinine ratio than the sham surgery group and the AXT914 administration groups, whereas there was no difference between the sham surgery group and the AXT914 administration groups.

2-2. Effects of AXT914 in Total Parathyroidectomy and Auto-Transplantation Model (Experimental Schedule 2)

Using rat blood collected before drug administration as a baseline, serum PTH, calcium, and phosphorus levels of the sham surgery group, the vehicle administration group, and the AXT914 administration group were compared on Day 21 and Day 28 after the start of drug administration, and the results were illustrated in FIG. 4.

The PTH and calcium levels were lower and the phosphorus levels were higher in the vehicle administration group than in the sham surgery group. In the AXT914 administration group, the PTH levels on Day 21 after drug administration were lower than those in the sham surgery group, but significantly higher than those in the vehicle administration group. In the AXT914 administration group, the calcium levels on Day 21 after drug administration were significantly higher than those in the vehicle administration group, and there was no difference from those in the sham surgery group. On day 28 (7 days after drug discontinuation), the calcium levels in the AXT914 administration group were lower than those in the sham surgery group, but still higher than those in the vehicle administration group. In the AXT914 administration group, the phosphorus levels on Day 21 after drug administration were significantly lower than those in the vehicle administration group, and there was no difference from those in the sham surgery group. On day 28 (7 days after drug discontinuation), the phosphorus levels in the AXT914 administration group were lower than those in the vehicle administration group, but there was no statistical difference.

2-3. Effects of AXT914 in Total Parathyroidectomy and Auto-Transplantation Model (Experimental Schedule 3)

The parathyroid tissues transplanted into the SCM muscles of the vehicle administration group and the AXT914 administration groups were observed by H&E staining and immunohistochemistry.

As a result of H&E staining, the area of transplanted parathyroid tissue was increased in AXT914 administration groups 1 and 2 compared to the vehicle administration group. AXT914 administration group 1 showed a 36% area increase, and AXT914 administration group 2 showed a significant area increase of about 3 times (FIG. 5). From these results, it can be seen that the administration of AXT914 contributes meaningfully to the successful engraftment of transplanted parathyroid tissues.

As a result of immunohistochemical staining, PTH, VEGFA, and CD31 expressions were significantly increased in parathyroid tissues in AXT914 administration groups 1 and 2 compared to the vehicle administration group (FIGS. 6*a* and 6*b*). In AXT914 administration groups 1 and 2, the expression level of PTH was increased about 2-fold compared to that in the vehicle administration group. To confirm the formation of blood vessels and vascular permeability, and the like, the results of confirming the expression of VEGFA, CD31, and FGF2 showed a significant increase of about 6-fold and about 10-fold in the expression of VEGFA in AXT914 administration group 1 and AXT914 administration group 2, respectively. The number of CD31 positive cells was increased about 3 folds in AXT914 administration group 1 and about 4.5 folds in AXT914 administration group 2 compared to the vehicle administration group. FGF2 positive cells, which are growth factors involved in angiogenesis, were not statistically significant, but showed an increasing pattern in the AXT914 administration groups. From these results, it can be seen that the administration of AXT914 after damage to and transplantation of the parathyroid tissue contributes considerably to the neovascularization and angiogenesis, and the enhancement of vascular permeability. The expression of MCL1, which functions to promote cell survival, was not statistically significant in AXT914 administration group 2, but showed an increasing pattern. The expression of Ki67, which is a marker of cell proliferation, was not different between the administration groups, so that it can be seen that AXT914 does not particularly affect cell proliferation.

From the above results, it can be seen that the administration of AXT914 significantly restores the function of the parathyroid tissue by stimulating and promoting angiogenesis of the transplanted parathyroid tissue.

In conclusion, it can be seen that when the parathyroid gland is damaged and partially removed or the removed parathyroid gland is re-transplanted, administration of a CaSR antagonist, such as AXT914, restores the function of the parathyroid tissue, and thus the PTH secretion function is improved.

What is claimed is:

1. A method for promoting the engraftment of transplanted parathyroid tissues through neovascularization and angiogenesis in a mammal in need of functional restoration of a damaged parathyroid gland, the method comprising administering to the mammal a composition comprising a calcium-sensing receptor antagonist compound of Formula 1:

[Formula 1]
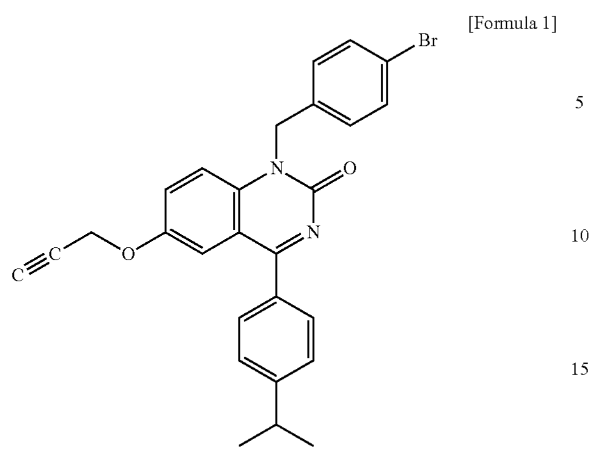
as an active ingredient,
wherein the composition is orally administered at a concentration of 10 to 30 mg/kg.
* * * * *